United States Patent [19]

Mayer

[11] Patent Number: 4,614,000
[45] Date of Patent: Sep. 30, 1986

[54] PATIENT UNDERSHEET FOR PREVENTING BED SORES

[75] Inventor: Nathan Mayer, E. Brunswick, N.J.

[73] Assignee: Pacon Manufacturing Corp., Metuchen, N.J.

[21] Appl. No.: 622,111

[22] Filed: Jun. 19, 1984

[51] Int. Cl.[4] .......................... A61G 7/04; B32B 3/22
[52] U.S. Cl. .......................................... 5/484; 5/468; 5/455; 5/502
[58] Field of Search .................. 5/484, 482, 487, 468, 5/455, 449, 458, 420, 500, 502

[56] References Cited

U.S. PATENT DOCUMENTS

| 3,446,692 | 5/1969 | Turnbull . | |
|---|---|---|---|
| 3,468,311 | 9/1969 | Gallagher | 5/458 |
| 3,523,055 | 8/1970 | Lemelson . | |
| 3,574,873 | 4/1971 | Weinstein | 5/450 |
| 3,646,624 | 3/1972 | Zipf | 5/484 |
| 3,756,884 | 9/1973 | Hagino . | |
| 3,812,001 | 5/1974 | Ryan | 5/484 |
| 3,876,741 | 4/1975 | Klein . | |
| 3,921,232 | 11/1975 | Whyte . | |
| 3,974,532 | 8/1976 | Ecchuya . | |
| 3,989,867 | 11/1976 | Sisson | 5/484 |
| 4,018,034 | 4/1977 | Keren . | |
| 4,018,946 | 4/1977 | Klein . | |
| 4,074,505 | 2/1978 | Keren et al. . | |
| 4,099,269 | 7/1978 | Porner . | |
| 4,270,658 | 6/1981 | Schuster . | |
| 4,378,391 | 3/1983 | Allen . | |
| 4,472,472 | 9/1984 | Schultz | 5/449 |

FOREIGN PATENT DOCUMENTS 2221725  11/1973  Fed. Rep. of Germany .......... 5/455

Primary Examiner—Alexander Grosz
Attorney, Agent, or Firm—Richard C. Woodbridge

[57] ABSTRACT

A patient care undersheet includes a minimum number of support points in order to keep a bedridden patient from developing decubitus ulcers. The undersheet preferably comprises a bottom layer having a number of conically shaped bubble-like supports and a top layer comprising a non-woven fabric. An adhesive material connects the non-woven fabric to the bubble-like supports in such a manner that under pressure the bubble-like supports under pressure do not move with respect to each other. The bubble-like supports are air tight so that the undersheet does not collapse under the pressure of a patient's body. The area of contact of the top of the bubble-like supports to the non-woven fabric is approximately 40% of the total top surface of the undersheet. A patient only has to move a very small distance before a new area of skin is supported by the undersheet.

17 Claims, 6 Drawing Figures

PATIENT UNDERSHEET FOR PREVENTING BED SORES

BACKGROUND OF THE INVENTION

1. Field of the Invention

The invention relates to an undersheet comprising a bottom layer having a plurality of bubble-like supports and a top layer made from a non-woven fabric for use in preventing bed sores in bedridden patients.

2. Description of the Prior Art

The problem of bed sores (decubitus ulcers) is a medical dilemma that has plagued mankind for centuries. The problem arises in bedridden patients when the small capillaries in the skin are under constant pressure. This is common for patients with bone fractures or diseases which take a long time to treat. Continual compression of the capillaries causes them to close down and the flow of blood ceases. The dead cells created in the process break through the surface of the skin forming sores. Sores up to and exceeding $2\frac{1}{2}''$ in diameter have been recorded. Decubitus ulcers generally can not be seen in the developmental stage. Therefore, detection is only possible in later stages—after it is too late to prevent. As a rule of thumb bed sores take approximately two weeks to form and may take as many as two years to get rid of. The bed sore problem is of special concern in today's economy for two major reasons. First, the population is getting older and health care is getting better. Therefore, more people are spending more time in hospital beds. Second, there is an accute shortage of nursing care in proportion to the need. That means there are fewer hospital personnel to turn and massage patients on a regular basis. The combined effect is that there are fewer people to tend more bed ridden people. Therefore, there is a clear need for a means to prevent bed sores which doesn't require additional manpower. Attempts have been made in the past to prevent bed sores.

For example, U.S. Pat. Nos. 3,574,873 and 3,974,532 both describe rubberized mattress products designed to minimize decubitis. In particular, the apparatus described in U.S. Pat. No. 3,974,532 is directed towards a mechanism for promoting ventilation to prevent problems such as "prickly heat".

There are a number of prior art patents directed towards products which include air tight bubbles or blisters. U.S. Pat. Nos. 3,392,081 and 3,661,155 owned by the Sealed Air Corporation are directed towards air filled bubble sheets that don't leak air.

There are also certain prior art devices that employ materials having a plurality of bubbles or blisters in a medical context. The structure described in U.S. Pat. No. 3,812,001 calls for a substrate including a plurality of "air-filled blisters" covered by a top surface. The top surface can be "comprised of a soft woven or a non-woven fabric-like tissue". It is important to note that the structure in U.S. Pat. No. 3,812,001 discloses an "absorbent layer" between the upper layer and the bottom layer. It is believed that the structure shown in U.S. Pat. No. 3,812,001 would not be helpful in minimizing decubitis because the "absorbent layer" would substantially interfere with the flow of fresh air through the material. In addition, it would tend to further distribute the weight of the patient over the entire surface rather than at discrete points.

U.S. Pat. No. 3,468,311 describes another pad which includes perforations for liquids to pass through a layer of air cells to an absorbent layer below. However, the structure disclosed in that patent is not believed to be as effective as the present structure in preventing decubitis ulcers. First, there is no top layer to keep the cell tops from spreading out. Second, by retaining moisture in an absorbent lower pad there is a greater tendency toward skin irritation. Third, there isn't as great as air circulation. Fourth, it is noted that the top area of the air cells in U.S. Pat. No. 3,468,311 is very large therefore making a lot of contact with the skin of the patient. This is exactly the opposite of the purpose and structure of the present invention which is to provide minimal skin support contact. Fifth, and last, a primary purpose of the "Absorbent Pad" of U.S. Pat. No. 3,468,311 appears to be to act as a cushion for the patient. That is not the primary purpose of the undersheet of the present invention which is used to prevent the formation of decubitis ulcers.

U.S. Pat. No. 3,756,884 is of general interest in that is discloses a bubble-type substrate covered by a top film which can be adhered to an intermediate film producing a composite structure. Other than that, the foregoing reference does not appear to be relevant to the present invention. Likewise U.S. Pat. No. 4,099,269 shows a medical device which comprises layers of bubble material. Similarly, U.S. Pat. No. 4,270,659 discloses another medical device employing blister-like materials having certain breathable characteristics.

While the prior art discloses some individual features of interest, none of it, taken singularly or in combination anticipates applicant's novel structure for preventing the miseries of decubitis.

SUMMARY OF THE INVENTION

Briefly described the invention comprises a patient care undersheet including a minimum number of support points to keep a bedridden patient from developing decubitis ulcers. The undersheet comprises a bottom layer having a large number of conically shaped, bubble-like supports and a top layer comprising a non-woven fabric. The bubble-like supports are air tight so that they don't lose their inflated shape. Each bubble-like support includes a top portion which is adhesively attached to the non-woven fabric. The non-woven fabric is relatively porous allowing air to pass therethrough. Rayon ® or polyester or a combination of both held together by an adhesive may be incorporated into the non-woven fabric. The area of contact of the top of the bubble-like supports with respect to the non-woven fabric is approximately 40% of the total surface area of the undersheet. Air circulation channels are formed in the space between the non-woven fabric top sheet and the bottom layer. The air channels promote vigorous air circulation to the approximately 60% of the patient's skin that is not supported by the tops of the bubble-like supports. The fact that only approximately 40% of the skin of the patient comes into contact with the tops of bubble-like supports is important. This feature allows the patient to move only a very small distance before a new area of skin is exposed to the fresh air circulating through the air channels in the undersheet. For example, if the top of an air cell support is only $\frac{1}{4}''$ in diameter and the cells are on $\frac{1}{2}''$ centers then the patient only has to move a scant $\frac{1}{8}''$ for the supported area of the skin to translate 100% to an area of non-support, i.e. non direct contact. Therefore, minor movements of the patient result in major shifts in skin contact points. Moreover, that slight movement produces a relatively vigorous massaging action because of the great shift in pressure from contact point to non-contact point. Massage is helpful to the blood circulation. However, the weight of the body is distributed over so many discrete bubble-like supports that the bubble-like supports never feel uncomfortable to the patient. For example, if a patient weighs 200 pounds and is supported by a sheet measuring 36" long×24" wide, then the average loading per square inch is only 0.231 lbs./sq.in. That is a relatively low pressure and highly acceptable to the average patient. Substantial air circulation through the air channels cooperate to minimize the chance of a patient developing decubitis ulcers.

The invention can be more fully understood by reference to the following drawings and the detailed description of the preferred embodiment of the invention.

DETAILED DESCRIPTION OF THE PREFERRED EMBODIMENT

During the course of this description like numbers will be used to identify like elements according to the different figures which illustrate the invention.

Figure 1:
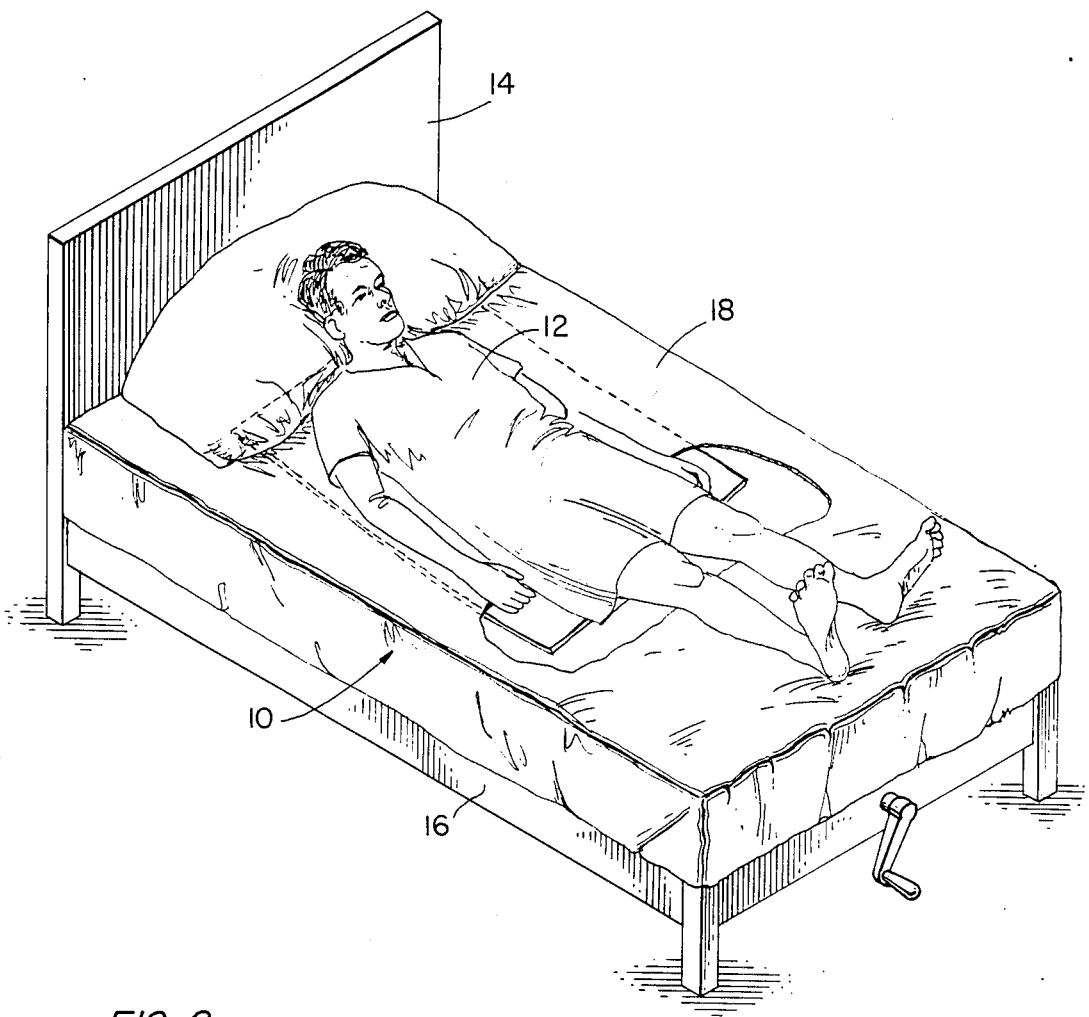
FIG. 1 is a perspective view showing the positioning of the undersheet invention with respect to a bedridden patient.

FIG. 1 shows the manner in which the invention 10, according to the preferred embodiment thereof, is used with respect to a bedridden patient 12. Patient 12 is shown in FIG. 1 as resting in a bed 14 which includes a mattress 16 covered by conventional bed sheet 18. Undersheet 10 is preferably approximately 2 ft. wide by 3 ft. long. It is generally located under bed sheet 18 and beneath the points of maximum contact with the patient's body. The points of maximum contact would typically extend from the shoulders to below the buttocks. It is preferable to place undersheet 10 under bed sheet 18 because the undersheet 10 is somewhat noisy and because the bed sheet 18 holds the undersheet 10 down therefore keeping it from crumpling and curling. While undersheet 10 is shown under bed sheet 15 it should be understood that it could also be located directly under the patient 12.

Figure 2:
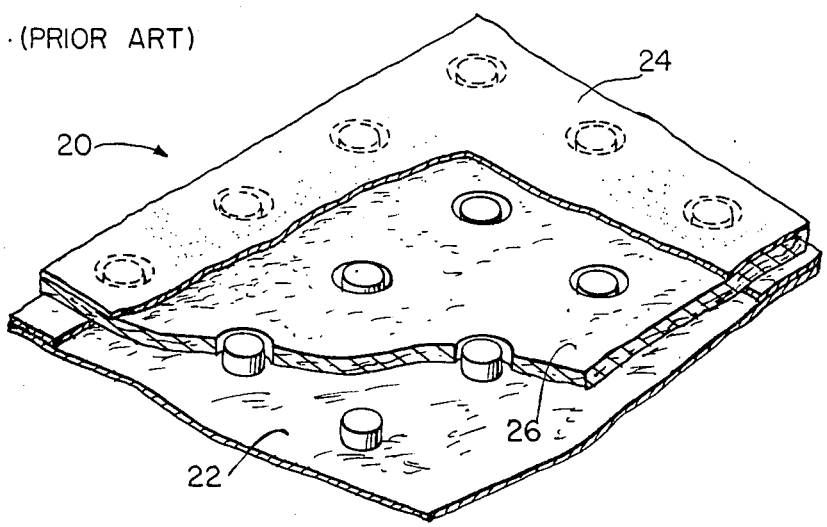
FIG. 2 shows a prior art apparatus used as a diaper.

A prior art diaper invention 20 is illustrated in detail in FIG. 2. A bottom layer 22 including a plurality of blisters is located directly below a top layer 24. An absorbent layer of material 26 occupies substantially all of the space between bottom layer 22 and top layer 24. Absorbent layer 26 is designed to collect urine and other liquids in a diaper-like fashion. The structure illustrated in FIG. 2 is described in further detail in U.S. Pat. No. 3,812,001. Other prior art devices of possible interest are also described in the portion of this disclosure entitled "Description of the Prior Art." The major problem with prior art structure 20 is that the presence of absorbent layer 26 further distributes the support of the patient's body. Accordingly, it is believed that the effect of using a prior art structure 20 such as illustrated in FIG. 2 would be to increase the likelihood of developing decubitis ulcers rather than decrease the likelihood. First of all, the distributed support of the air blisters plus the absorbent layer would mean that the patient was continually in contact over effectively 100% of the body rather than over selected portions of the sheet thereby making it impossible for the patient to expose a portion of the body to a non-supported area. This would also tend to minimize any beneficial massaging action the pad might generate. Second, the lack of air circulation increases the likelihood of bed sores. Third, the presence of trapped moisture in layer 26 would tend to hasten the advent of "diaper rash" or similar afflictions. Accordingly, all of the prior art devices identified do not appear to have the same ability to minimize the tendency towards decubitis ulcers as the preferred embodiment of the invention.

Figure 3:
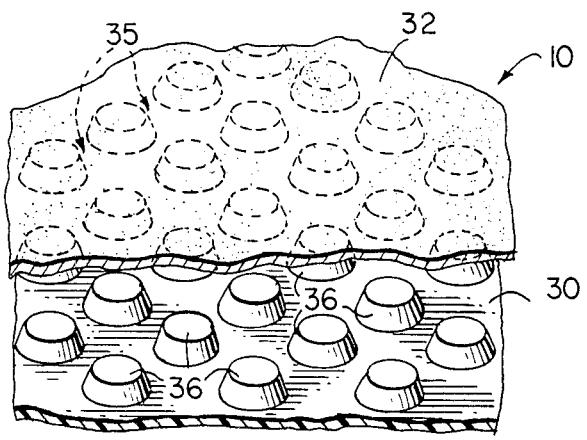
FIG. 3 is a perspective view of the preferred embodiment of the invention showing the top layer cut away to expose the bottom layer.

The preferred embodiment of the invention is described in detail in FIGS. 3, 4, 5, and 6. A partial cutaway of the invention 10 is illustrated in FIG. 3. Undersheet 10 essentially comprises a bottom layer 30 and a top layer 32 separated by bubble-like structures 36. Top layer 32 is attached to the top 46 of bubbles 36 by an adhesive medium 34. The space between bottom layer 30 and top layer 32 defines a plurality of air circulation channels 35. Air circulation channels 35 permit air to freely flow from the edge of undersheet 10 or through the relatively porous top layer 32 into channels 35 and out again through top layer 32 thereby keeping fresh, circulating air continually in contact with the skin of patient 12. The movement of patient 12 over the undersheet 10 also tends to "pump" air from one portion of undersheet 10 to another. Patient movement also provides a natural messaging action as the skin of the patient is randomly supported at various different points over a given period of time.

Figure 6:
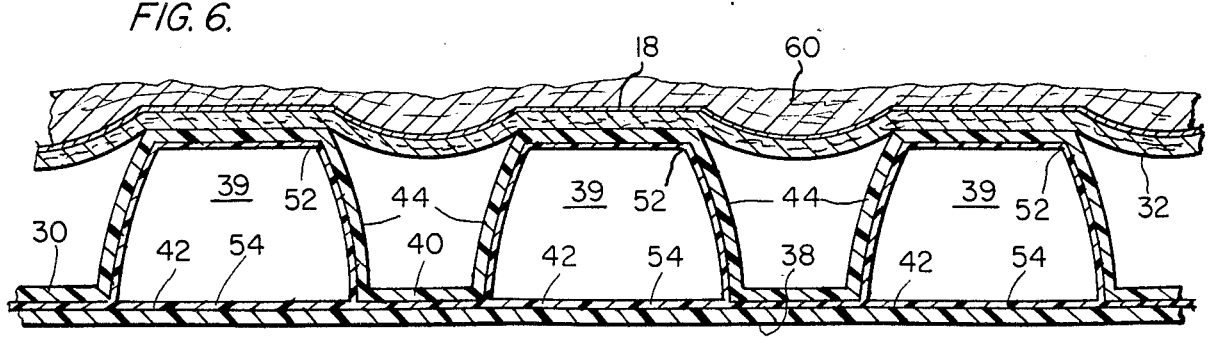
FIG. 6 is a detailed cross-sectional view of the wall structure of a single bubble-like support.

The structure of bottom layer 30 is relatively important with respect to the overall performance of undersheet 10. As shown in FIG. 6 the bottom layer 30 preferably comprises a lower layer 38 and a top layer 40 which traps an air bubble 39 in between the two layers. Each bubble 36 includes a relatively broad base 42, tapered conical sides 44 and a top 46 having an area less than the area of base 42. An air tight sealing material 52 may also be included in the air cavity 39 as shown in FIG. 6. It is important that the bubbles 36 be relatively air tight so that they do not collapse under the weight of a patient 12. If bubbles 36 were to collapse, then air circulation channels 35 would also collapse resulting in poor ventilation to the skin of the patient 12. Moreover, the area of contact between the sheet 10 and the patient 12 would increase as the bubbles became more and more squashed. That also would be undesirable for reasons previously explained. The conical sides 44 of the bubbles 36 also serve another important function. It has been found that conical bubbles 36 are stronger than bubbles having cylindrical side walls or side walls of other shapes. First of all, it is noted that the conical side walls 44 have less of a tendency to burst than would conventional cylindrical side walls. Secondly, conical side walls provide better support for the top area 46 of the bubbles 36 since the general shape of the bubbles 36 is that of a pyramid. While conically-shaped bubbles are preferred it is noted that cylindrically-shaped bubbles will also work under some circumstances though not as well.

Figure 4:
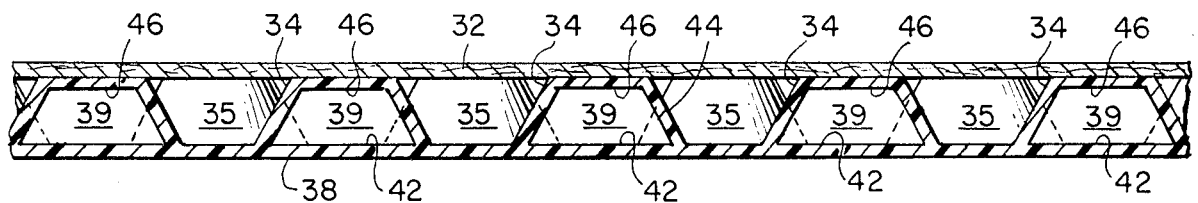
FIG. 4 is a side elevation, cross-sectional view of the preferred embodiment of the invention shown in FIG. 3.
Figure 5:
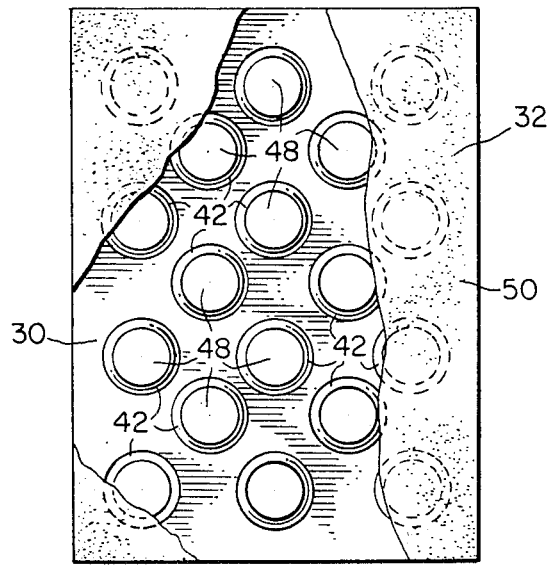
FIG. 5 is a top plan view of the preferred embodiment of the invention shown in FIG. 3 illustrating the amount of area occupied by the contact points between the upper non-woven sheet and the top of the bubble-like supports.

Another important feature of the invention is illustrated in detail in FIG. 5. The top 46 of each bubble 36 has an area of contact 48 with top layer 32. Contact area 48 is secured by an adhesive medium 34 as previously described and as shown in FIG. 4. The entire surface of top layer 32 can be defined as either areas of contact 48 or areas of non-contact 50 all of which combine to comprise the entire surface. According to the preferred embodiment, the area of bubble contact 48 comprises roughly 40% of the entire surface of the top layer 32. In other words, the area of non-contact comprises approximately 60% of the surface of top layer 32. The foregoing is important for several reasons. First, the relatively small contact ratio (i.e. 40%) means that a patient 12 only has to move a very small distance in order to move the skin from an area of support 48 to an area of relative non-support 50. Since decubitis ulcers are brought on in part by direct pressure on the skin, the preferred embodiment of the invention 10 provides a means for minimizing the area of contact with the skin of a patient 12. Second, the adhesive 34 attaches each of the tops of the bubbles 46 to each other by upper layer 32. Therefore, each of the bubbles 36 tend to cooperate and jointly support each other. Adhesive 34 also prevents the bubbles 36 from shifting away from each other. According to the preferred embodiment the diameter of contact area 48 is approximately ¼". Movement by patient 12 of approximately ⅛" brings the skin of the patient 12 into contact with a non-support area 50, thereby minimizing the chances of developing decubitis ulcers. According to the preferred embodiment the diameter of contact area 48 is approximately 3/16" with a preferred acceptable range of from ⅛" to ⅜" in diameter. The preferred diameter of the base 42 is ¼" with a preferred range of 3/16" to ⅜". The bubble-like supports 36 are preferably arranged on ½" centers and staggered every other row in a diamond like pattern. Sheet depth measured from the top 46 to the base 42 of each bubble-like support 36 is preferably 3/16" with a preferred range of ⅛" to ¼" in height. While not preferred, it is possible to produce sheets having bubble-like supports 36 with a 1" base 42 and a ¾" top 46 which might be acceptable under special circumstances. The ratio of contact between the contact areas 48 and non-contact area 52 is 40:60 and the preferred range of contact areas 48 is 20% to 60% of the total area.

In FIG. 6 the skin 60 of patient 12 is shown in contact with upper layer 32. Skin 60 is supported at contact points 48. In between contact points 48 the upper layer 32 sags under the weight of patient 12. In other words the patient is supported by contact areas 48 and is not supported by non contact area 50. When the patient 12 is not in contact with undersheet 10 the uper layer 32 is relatively flatter as shown in FIG. 4. As patient 12 moves over the undersheet 10 the upper layer 32 undulates causing fresh air to pump throughout the system.

The film comprising the bottom layer 30 is approximately 0.001" thick. The conical sidewalls 44 are structurally superior to cylindrical sidewalls because cylindrical sidewalls tend to grow (i.e. expand) more under pressure than do conical sidewalls. Therefore, cylindrical sidewalls are more likely to burst since they then to stretch more than conical sidewalls. As previously described, it is desirable that the bubbles 36 be air tight so as to retain the air captured within the cavity 39 of the bubbles 36. Technology already exists to keep the bubbles 36 air tight. See, for example, U.S. Pat. Nos. 3,392,081 and 3,661,155 owned by The Sealed Air Corporation and previously discussed in the "Description of the Prior Art". It is possible, for example, to treat the polyethylene material, which is preferred, to keep it from leaking air.

In order to improve the adhesive contact of the top 46 of the bubbles 36 with the top layer 32, it is generally desirable to employ an electronic discharge system to create a corona that roughs up the top surface 46 of the bubbles 36. This is a technique already known in the art. Adhesive 34 may include a solvent base adhesive-like urethane or, alternatively, could be a water based material such as acrylics or urethanes.

The top layer 32 preferably comprises a non-woven fabric including strands of a reinforcing material such as Rayon ® and/or polyester. The characteristics of top layer 32 are such that the top layer 32 must provide for substantial air circulation and be relatively strong so as not to fall under the weight of the patient 12. The circulation of air is encouraged by the nature of the non-woven materials used. The preferred non-woven material offers only 2% resistance to air flow which means that the air passes through the top layer as though it wasn't there. Accordingly, maximum air flow is achieved without sacrificing support for adjacent bubble-like supports 36. The type of non-woven material employed as a top layer 32 is generally referred to as "diaper facing" by the industry. It would be possible to use woven materials, however, non-woven materials are preferable because they are less expensive and have less resistance to air movement.

In summary, the present invention has numerous advantages over prior art devices. First, the undersheet 10 provides a limited area of direct support contact 48 between the patient 12 and the undersheet 10. This is because contact area 48 comprises approximately 40% of the total area of upper layer 32. If the width of the top 46 of bubbles 36 is approximately ¼", then only ⅜" movement by patient 12 will cause the skin of patient 12 to be exposed to a non-supported area 50. Second, the air channels 35 provide for a substantial flow of air. The air enters through the edges of the sheet 10 or through top layer 32 and circulates through channels 35 to other areas of the patient's 12 skin. Third, the undersheet 10 is relatively inexpensive to manufacture and is disposable. Fourth, because of channels 35 the undersheet 10 does not collect urine or other materials that would inhibit the circulation of air through the undersheet 10. Fifth, undersheet 10 is preferably 2 ft.×3 ft. in size. It is easy for an inexperienced attendant or nurse to change the undersheet 10. In general it is not necessary to completely remake a bed in order to change undersheet 10. Sixth, due to the air tight structure of bubbles 36, sheet 10 does not readily collapse. Moreover the use of adhesives 34 to attach top layer 32 to the top area 46 of bubbles 36, produces the result that adjacent bubbles 36 tend to support each other. Therefore, adjacent bubbles 36 do not tend to move away from each other but, on the contrary, tend to uniformly support the patient's weight. Seventh, the structure of the undersheet is such that it produces a natural "pumping" and "massaging" action that is very beneficial to the patient. The natural "pumping" action encourages the flow of fresh air to the skin of the bedridden patient and the natural massaging action is believed to stimulate blood flow.

While the invention has been described with reference to the preferred embodiment thereof, it will be appreciated by those of ordinary skill in the art that various modifications can be made to the structure of the invention without departing from the spirit and scope thereof.

I claim:

1. An undersheet apparatus for the prevention of bed sores in bedridden patients, said apparatus comprising:
   a base layer having a plurality of substantially air tight bubble-like supports each having a top which is relatively smller than a bottom and cone-shaped sides, the bottoms of said bubble-like supports being connected together such that the diameter of the top of said bubble-like supports is approximately 3/16", the distance between the top and bottom of said bubble-like supports is approximately 3/16" and the diameter of the bottom of said bubble-like supports is approximately ¼", said bubble-like supports being formed from a polyethylene material having a laminated structure comprising at least two layers;
   a relatively porous upper layer comprising a sheet of non-woven material, the air resistance of said upper layer being approximately 2%; and,
   adhesive means for attaching said upper layer to the top of said bubble-like supports.

2. An undersheet apparatus for the prevention of bed sores in bedridden patients, said apparatus comprising:
   a base layer having a plurality of bubble-like supports each having a closed top and a bottom and a side, the bottoms of said bubble-like supports being connected together;
   a relatively porous upper layer having an air resistance of approximately 2%; and,
   adhesive means for attaching said upper layer to the top of said bubble-like support so that air channel circulation means are formed between said upper layer and said base layer for circulating air through said porous upper layer, a plurality of patient contact areas being formed substantially at the locations where said upper layer is ahdesively connected to the tops of said bubble-like supports,
   wherein said patient contact areas carry substantially all of the force exerted by the patient on the apparatus thereby producing a massaging-like stimulation of said patient.

3. The apparatus of claim 2 wherein:
said upper layer comprises a sheet of non-woven material.

4. The apparatus of claim 3 wherein:
the area of the top of said bubble-like supports is between 20% and 60% of the total surface area of said porous upper layer.

5. The apparatus of claim 4 wherein:
the distance between the top and bottom of said bubble-like supports is in the range of ⅛" to ¼".

6. The apparatus of claim 5 wherein:
the diameter of the top of said bubble-like supports is in the range of ⅛" to ⅜".

7. The apparatus of claim 6 wherein:
the diameter of the bottom of said bubble-like supports is in the range of 3/16" to ½".

8. The apparatus of claim 7 wherein:
the interiors of said bubble-like supports are substantially air tight.

9. The apparatus of claim 8 wherein:
said bubble-like supports have cone-like shaped sides and wherein said top is relatively smaller in diameter than said bottom.

10. The apparatus of claim 9 wherein:
said bubble-like supports are formed from a polyethylene material having a laminated structure comprising at least two layers.

11. The apparatus of claim 10 wherein:
the area of the top of said bubble-like supports comprises apporoximately 40% of the total surface area of said upper layer.

12. The apparatus of claim 11 wherein:
the diameter of the top of said bubble-like supports is approximately 3/16".

13. The apparatus of claim 12 wherein:
the distance between the top and the bottom of said bubble-like supports is 3/16".

14. The apparatus of claim 13 wherein:
the diameter of the bottom of said bubble-like supports is approximately ¼".

15. The apparatus of claim 2 wherein:
said bubble-like supports have cylindrical sides.

16. An undersheet apparatus for the prevention of bed sores in bedridden patients, said apparatus comprising:
   a base layer having a plurality of bubble-like supports each having a closed top and a bottom and a side, the bottoms of said bubble-like supports being connected together;
   a highly porous upper layer which permits air to pass from said base layer through said upper layer; and,
   adhesive means for attaching said upper layer to the top of said bubble-like support so that air channel circulation means are formed between said upper layer and said base layer for circulating air through said porous upper layer, a plurality of patient contact areas being formed substantially at the locations where said upper layer is adhesively connected to the tops of said bubble-like supports,
   wherein said patient contact areas carry substantially all of the force exerted by the patient on the apparatus thereby producing a massaging-like stimulation of said patient.

17. An undersheet apparatus for the prevention of bed sores in bedridden patients, said apparatus comprising:
   a base layer having a plurality of bubble-like supports each having a closed top and a bottom and a side, the bottoms of said bubble-like supports being connected together;
   an upper highly air-porous layer;
   adhesive means for attaching said upper layer to the top of said bubble-like supports so that air channel circulation means are formed between said upper layer and said base layer for circulating air through said porous upper layer, a plurality of patient contact areas being formed substantially at the locations where said upper layer is adhesively connected to the tops of said bubble-like supports,
   wherein said patient contact areas carry substantially all of the force exerted by the patient on the apparatus thereby producing a massaging-like stimulation of said patient.

* * * * *